(12) United States Patent
Sasaki

(10) Patent No.: US 7,087,014 B2
(45) Date of Patent: Aug. 8, 2006

(54) ENDOSCOPE SYSTEM HAVING AN AUXILIARY LIGHTING DEVICE

(75) Inventor: Masahiko Sasaki, Chiba (JP)

(73) Assignee: PENTAX Corporation, Tokyo (JP)

(*) Notice: Subject to any disclaimer, the term of this patent is extended or adjusted under 35 U.S.C. 154(b) by 244 days.

(21) Appl. No.: 10/706,080

(22) Filed: Nov. 13, 2003

(65) Prior Publication Data

US 2004/0102680 A1 May 27, 2004

(30) Foreign Application Priority Data

Nov. 22, 2002 (JP) ............................. 2002-338965

(51) Int. Cl.
*A61B 1/07* (2006.01)
*G02B 6/43* (2006.01)

(52) U.S. Cl. ................ 600/178; 600/181; 600/182; 362/555; 362/574

(58) Field of Classification Search ............. 600/178, 600/181, 182; 362/20, 250, 551, 554, 555, 362/574; 348/68
See application file for complete search history.

(56) References Cited

U.S. PATENT DOCUMENTS

| 4,410,929 A * | 10/1983 | Feinbloom et al. ......... 362/572 |
| 4,855,875 A * | 8/1989 | Onose et al. ............... 362/572 |
| 5,971,576 A * | 10/1999 | Tomioka et al. ............ 362/574 |
| 6,318,887 B1 * | 11/2001 | Matsumoto ................. 362/574 |
| 6,438,302 B1 * | 8/2002 | Utsui et al. ................. 385/117 |
| 6,477,403 B1 | 11/2002 | Eguchi et al. |
| 6,482,150 B1 | 11/2002 | Utsui |
| 6,602,186 B1 | 8/2003 | Sugimoto et al. |
| 2002/0045801 A1 * | 4/2002 | Niida et al. ................. 600/118 |

FOREIGN PATENT DOCUMENTS

| JP | 7-27012 | * | 5/1995 |
| JP | 2883083 | * | 2/1999 |
| JP | 11-305148 | | 11/1999 |
| JP | 2002-72106 | * | 3/2002 |

* cited by examiner

*Primary Examiner*—John P. Leubecker
(74) *Attorney, Agent, or Firm*—Greenblum & Bernstein, P.L.C.

(57) ABSTRACT

An endoscope system includes an endoscope having an insertion tube; a main light source; an auxiliary light source; and a fiber-optic light guide provided in the insertion tube, the fiber-optic light guide being provided with an incident end face which selectively faces one of the main light source and the auxiliary light source, and an exit end face which faces an illuminating optical system provided at a distal end of the insertion tube. The auxiliary light source is a white LED.

10 Claims, 9 Drawing Sheets

ENDOSCOPE SYSTEM HAVING AN AUXILIARY LIGHTING DEVICE

BACKGROUND OF THE INVENTION

1. Field of the Invention

The present invention relates to an endoscope system having an auxiliary lighting device which lights up in the event of failure in a main light source of the endoscope.

2. Description of the Related Art

In an endoscope system having an auxiliary lighting device, the incident end face of a fiber-optic light guide (a bundle of fibers) of the endoscope is connected to the lighting device. The incident end face of the fiber-optic light guide is positioned to face a main lamp provided in the lighting device, while the exit end face of the fiber-optic light guide is connected to an illumination lens provided at the insertion end of the flexible insertion tube of the endoscope. Illuminating light emitted from the main lamp is guided to the illumination lens through the fiber-optic light guide to be projected outwards from the illumination lens to illuminate an internal body cavity, or an internal cavity inside a machine. This structure is disclosed in, e.g., a Japanese laid-open patent publication NO.11-305148.

If the lighting device is provided with only one lamp, an endoscopic operation must be suspended in the event where the lamp goes out accidentally during the endoscopic operation. To prevent this problem from occurring, the lighting device is usually provided with an auxiliary lamp which lights up in the event of failure in the main lamp. The auxiliary lamp is retracted so as not to face the incident end face of the fiber-optic light guide in a normal state of the endoscope. In the event of accidental failure of the main lamp, the auxiliary lamp moves to its operating position, at which the auxiliary lamp faces the incident end face of the fiber-optic light guide, and lights up to supply illuminating light to the incident end face of the fiber-optic light guide.

However, in conventional endoscopes having such an auxiliary lamp, the service life of the auxiliary lamp is short consumes a large amount of power because a light source such as an xenon lamp which consumes a high amount of power is used as the auxiliary lamp.

SUMMARY OF THE INVENTION

The present invention provides an endoscope system having an auxiliary lighting device, wherein the service life of the auxiliary light source is semipermanent, and wherein the power consumption of the auxiliary light source can be minimized while a sufficient light quantity is ensured.

According to an aspect of the present invention, an endoscope system is provided including an endoscope having an insertion tube; a main light source; an auxiliary light source; and a fiber-optic light guide provided in the insertion tube, the fiber-optic light guide being provided with an incident end face which selectively faces one of the main light source and the auxiliary light source, and an exit end face which faces an illuminating optical system provided at a distal end of the insertion tube. The auxiliary light source includes a white LED.

It is desirable for the incident end face of the fiber-optic light guide to normally face the main light source, and face the auxiliary light source in the event of failure of the main light source.

It is desirable for the auxiliary light source to be movable between a retracted position where the auxiliary light source is aside from a position at which the auxiliary light source faces the incident end face of the fiber-optic light guide, and an operating position where the auxiliary light source faces the incident end face of the fiber-optic light guide. The auxiliary light source remains in the retracted position when the main light source is ON. The auxiliary light source moves to the operating position in the event of failure of the main light source.

It is desirable for the endoscope system to further include a positive lens positioned in front of the white LED so that the positive lens is positioned between the white LED and the incident end face of the fiber-optic light guide when the white LED is in the operating position. Light rays emitted from the white LED are converged through the positive lens to be incident on the incident end face of the fiber-optic light guide. The optical axis of the white LED is coincident with both an optical axis of the positive lens and an axis of the fiber-optic light guide when the white LED is in the operating position.

It is desirable for the front focus of the positive lens is coincident with a point of light emission of the white LED.

It is desirable for the following conditions (1), (2) and (3) to be satisfied:

$$r_1 \geq b \times \tan \theta_1 \quad (1)$$

$$(a-c)\tan\theta_2 = r_2 \quad (2)$$

$$\theta_3 \geq \theta_2 \quad (3)$$

wherein "a" designates the image distance of the positive lens; "b" designates the object distance of the positive lens; "c" designates the distance between a principle plane of the positive lens and the incident end face of the fiber-optic light guide; "$r_1$" designates the radius of the positive lens; "$r_2$" designates the radius of the incident end face of the fiber-optic light guide; "$\theta_1$" designates the exit angle of the light rays emitted from the white LED; "$\theta_2$" designates the angle of incidence of light rays which emerge from the positive lens to be incident on the incident end face of the fiber-optic light guide; and "$\theta_3$" designates the threshold angle of incidence of light rays on the incident end face which are transmittable through the fiber-optic light guide.

It is desirable for an effective aperture of the positive lens to be equal to a diameter of the incident end surface of the fiber-optic light guide. The front focus of the positive lens is coincident with a point of light emission of the white LED.

It is desirable for the endoscope system to further include a video processor in which the main light source and the auxiliary light source are provided.

It is desirable for the video processor to include a moving device for moving the white LED between the retracted position and the operating position.

In another embodiment, an endoscope system is provided, including an endoscope having an insertion tube; and a lighting system having a main lamp and a white LED serving as an auxiliary lamp. The endoscope includes a fiber-optic light guide provided in the insertion tube, an incident end face of the fiber-optic light guide normally facing the main lamp when a distal end of the insertion tube is plugged into a socket provided on the lighting system. The lighting system includes a moving device for moving the white LED between a retracted position where the white LED is aside from a position at which the white LED faces the incident end face of the fiber-optic light guide and an operating position where the white LED faces the incident end face of the fiber-optic light guide. The white LED remains in the retracted position when the main lamp is ON.

The moving device moves the white LED from the retracted position to the operating position in the event of failure in the main lamp.

It is desirable for the lighting system to be incorporated in a video processor.

The present disclosure relates to subject matter contained in Japanese Patent Application No.2002-338965 (filed on Nov. 22, 2002) which is expressly incorporated herein by reference in its entirety.

BRIEF DESCRIPTION OF THE DRAWINGS

The present invention will be described below in detail with reference to the accompanying drawings in which.

DESCRIPTION OF THE PREFERRED EMBODIMENT

Figure 1:
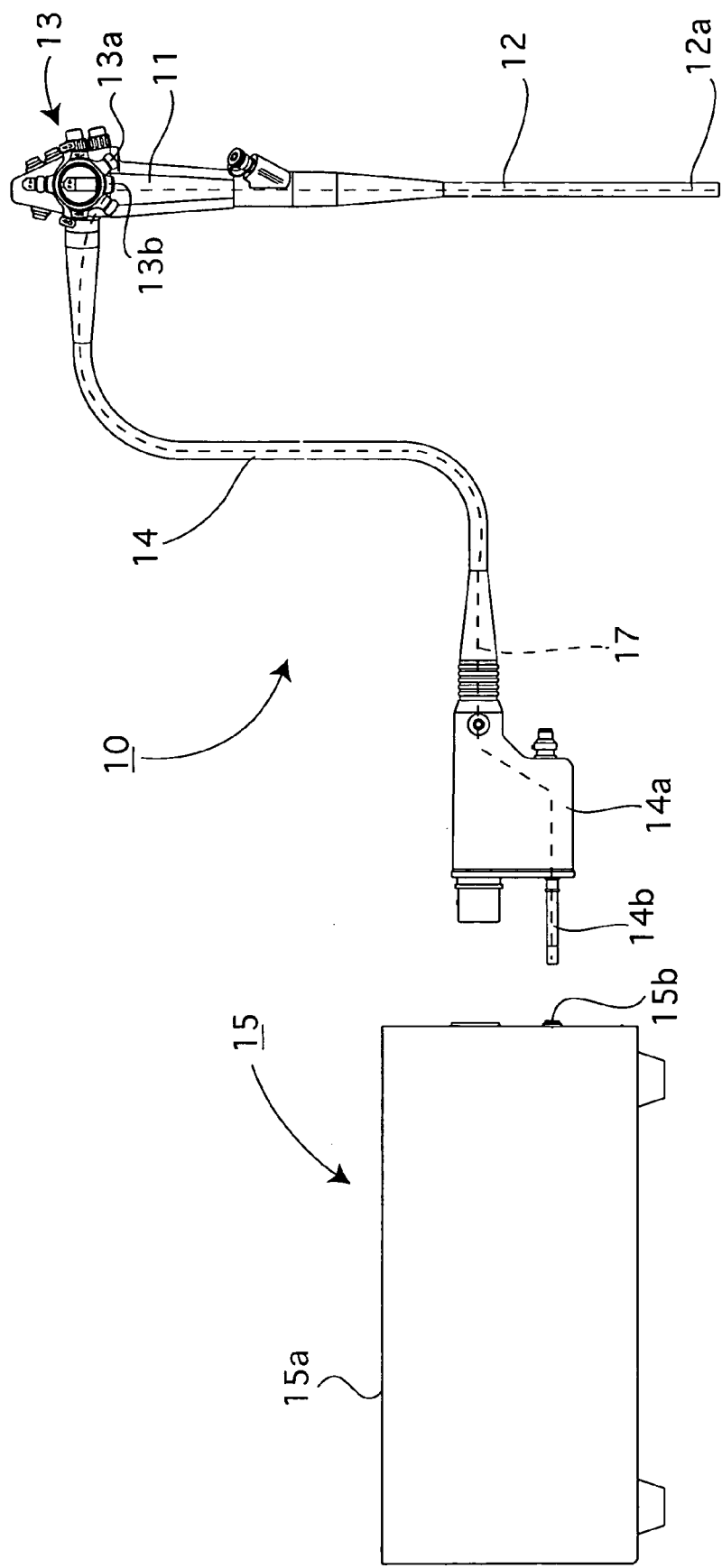
FIG. 1 is an external view of an embodiment of a video endoscope system which is composed of an endoscope and a video processor.

FIG. 1 shows an embodiment of a video endoscope system which is composed of an endoscope (fiber-optic endoscope) 10 and a video processor 15.

The endoscope 10 is provided with an operational body 11 and a flexible insertion portion (flexible insertion tube) 12 which extends from the control portion 11. The operational body 11 is provided thereon with a steering device 13 having a pair of angle knobs 13a and 13b. The distal end of the insertion portion 12 is formed as a (steerable) bendable portion 12a which can be steered to bend right, left, upward and downward by controlling the pair of angle knobs 13a and 13b of the steering device 13. The bendable portion 12a is provided at the tip thereof with an objective glass (not shown) and an illuminating lens (illuminating optical system; not shown).

The endoscope 10 is provided with a light-guide flexible tube (universal tube) 14 which extends from the operational body 11. The light-guide flexible tube 14 is provided at a distal end thereof with a connector 14a which is connected to the video processor 15.

As shown in FIG. 1, the video processor 15 is provided therein with a main lamp (main light source) 16. The main lamp can be, for example, a xenon lamp or a halogen lamp, etc. The main lamp 16 is switched ON and OFF when a switch (not shown) provided in the video processor 15 is switched ON and OFF, respectively. The main lamp 16 is made to remain ON when the insertion portion 12 is inserted into an internal body cavity, or an internal cavity inside a machine, etc.

Figure 7:
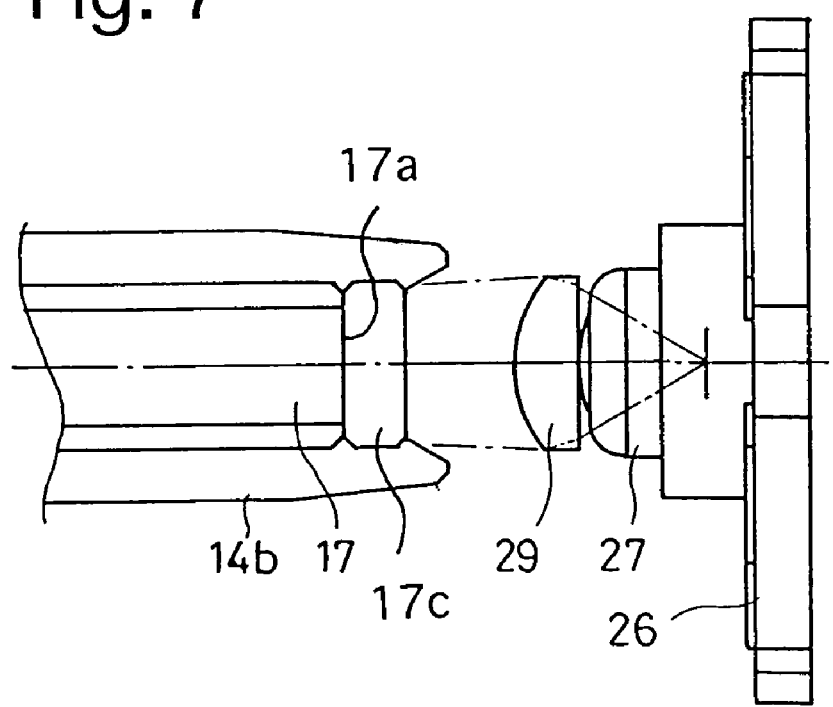
FIG. 7 is a side elevational view of the fundamental portion of the auxiliary lighting device shown in FIG. 6 and the incident end face of the fiber-optical light guide, showing the positional relationship among the white LED, the positive lens and the fiber-optic light guide when the white LED is in operation.

The endoscope 10 is provided with a fiber-optic light guide 17 (a bundle of optical fibers) which is positioned in the connector 14a, the light-guide flexible tube 14, the operational body 11 and the insertion portion 12 to extend from the connector 14a to the bendable portion 12a. An exit end face of the fiber-optic light guide 17 which is positioned in the bendable portion 12a in the vicinity of the tip thereof is connected to the aforementioned illuminating lens that is provided at the tip of the bendable portion 12a. A light guide plug 14b, in which the incident end of the fiber-optic light guide 17 is accommodated, projects from the connector 14a. As shown in FIG. 7, the light guide plug 14b is provided in the tip thereof with a protection glass 17c to which an incident end face 17a of the fiber-optic light guide 17 is connected. Note that the protection glass 17c is not shown in FIGS. 9 and 10 for the purpose of clarity. If the light guide plug 14b is plugged into a socket 15b (see FIG. 1) provided on a front panel of the video processor 15, the incident end face 17a of the fiber-optic light guide 17 faces the main lamp 16 with a predetermined distance between the incident end face 17a and the main lamp 16. In this state where the incident end face 17a faces the main lamp 16, illuminating light emitted from the main lamp 16 is transmitted to the aforementioned illuminating lens (which is provided at the tip of the bendable portion 12a) via the fiber-optic light guide 17 so that illuminated images of the object to be viewed via the aforementioned objective glass, which is provided at the tip of the bendable portion 12a, are indicated on a TV monitor (not shown) connected to the video processor 15.

The video processor 15 is provided therein with an auxiliary lighting device 18. The auxiliary lighting device 18 supplies illuminating light to the incident end face 17a of the fiber-optic light guide 17 in the event of failure in the main lamp 16 during an endoscopic operation in which the insertion portion 12 is inserted into a an internal body cavity, or an internal cavity inside a machine, etc.

The structure of the auxiliary lighting device 18 will be hereinafter discussed. The auxiliary lighting device 18 is provided with a fixing plate 19 which is fixed to a top wall of a casing 15a of the video processor 15 so that a major portion of the fixing plate 19 extends in a direction orthogonal to the light guide plug 14b (in a vertical direction as viewed in FIG. 2). The fixing plate 19 is provided at a lower end thereof with a horizontal plate 20 which extends forwards (rightward as viewed in FIG. 2) from the lower end of the fixing plate 19 in a direction parallel to the light guide plug 14b, and is further provided with a vertical plate 21 which extends downwards from one end (right end as viewed in FIG. 2) of the horizontal plate 20 in a direction parallel to the fixing plate 19.

The auxiliary lighting device 18 is provided with a rotary solenoid S which is electrically connected to a controller (not shown) provided in the auxiliary lighting device 18. The auxiliary lighting device 18 is provided behind the rotary solenoid S with a rotatable member 22 which is pivoted on a rotary shaft (output shaft; not shown) of the rotary solenoid S. The rotatable member 22 is in the shape of a teardrop-shaped plate, and is provided with a disc portion 23 and an arm portion 24 which projects from an outer end of the disc portion 23 in a radial direction of the disc portion 23, wherein the arm portion 24 is in the shape of a substantially triangular plate. A central portion of the disc portion 23 is fixed directly to the rotary shaft of the rotary solenoid S.

A tongue portion 25 projects downwards from a central portion of a lower end of the horizontal plate 20. A pivot 25a (see FIG. 3) projects rearward from a central portion of a rear surface (the surface on the side of the main lamp 16) of the tongue portion 25.

Figure 3:
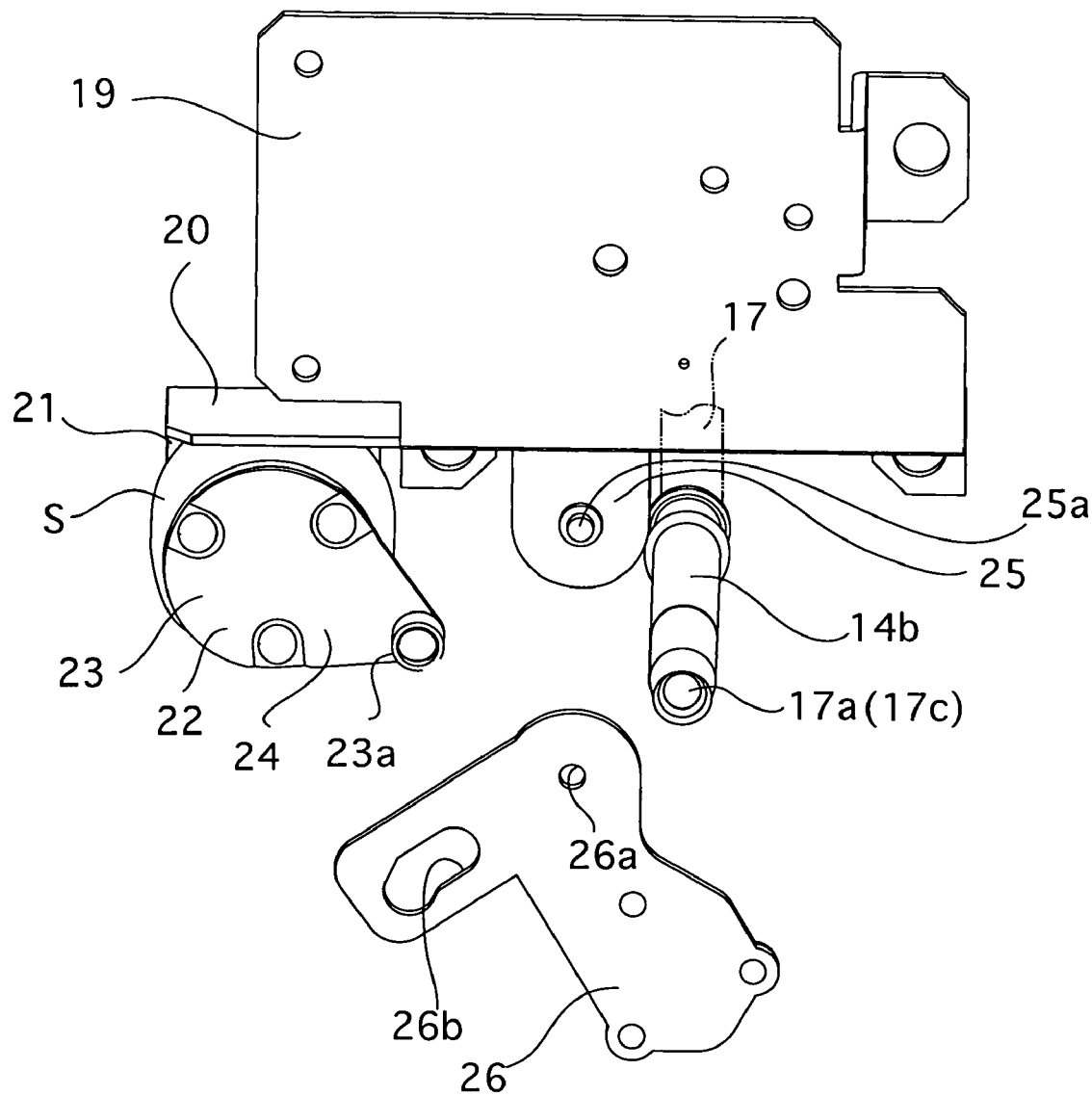
FIG. 3 is an exploded perspective view of the auxiliary lighting device shown in FIG. 2, seen from the side of the main lamp, in a state where a rotatable plate of the auxiliary lighting device is removed.
Figure 4:
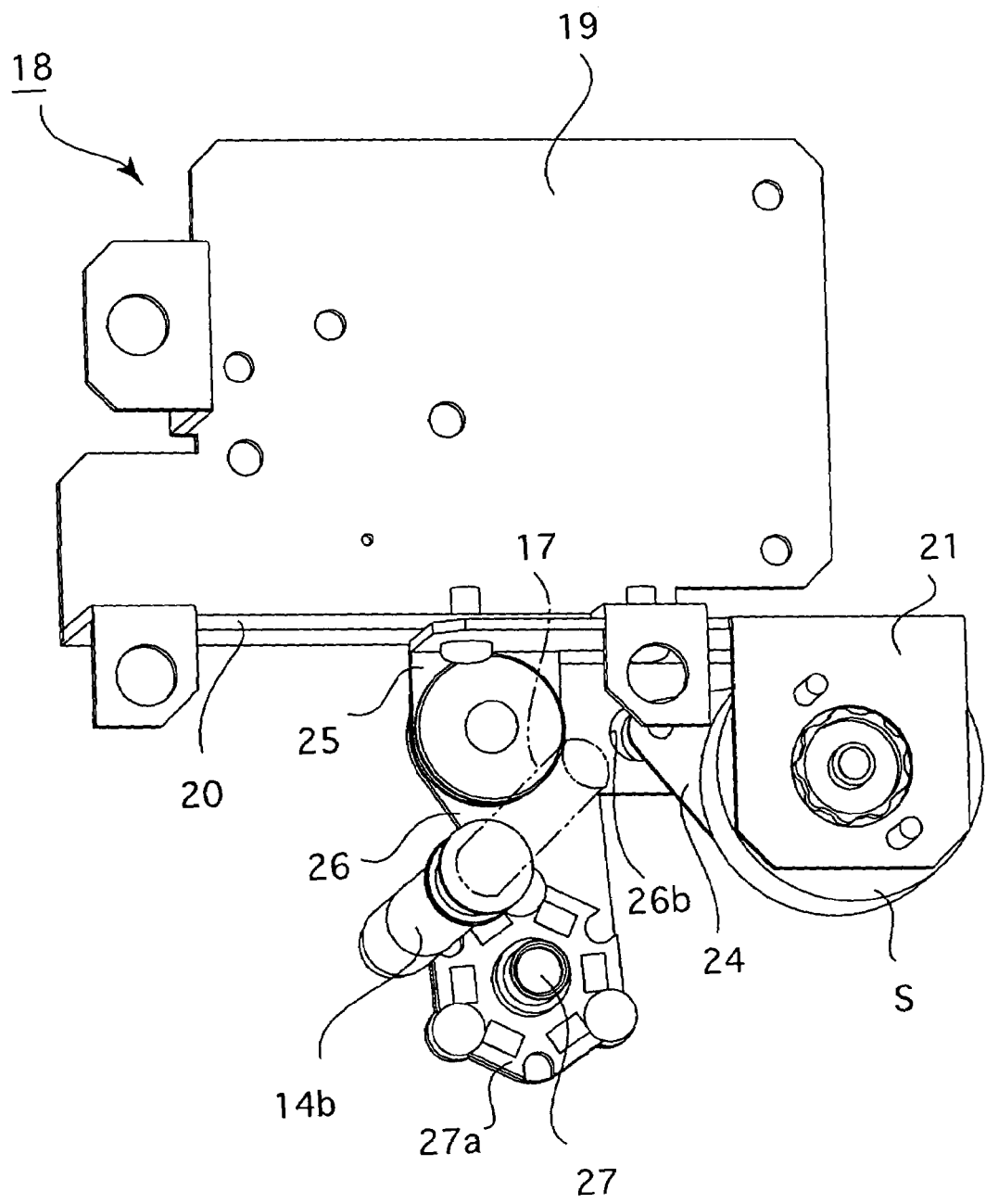
FIG. 4 is a perspective view of the auxiliary lighting device shown in FIG. 2, seen from the side of the fiber-optic light guide, in a state where the rotatable plate is in a non-operational position.
Figure 5:
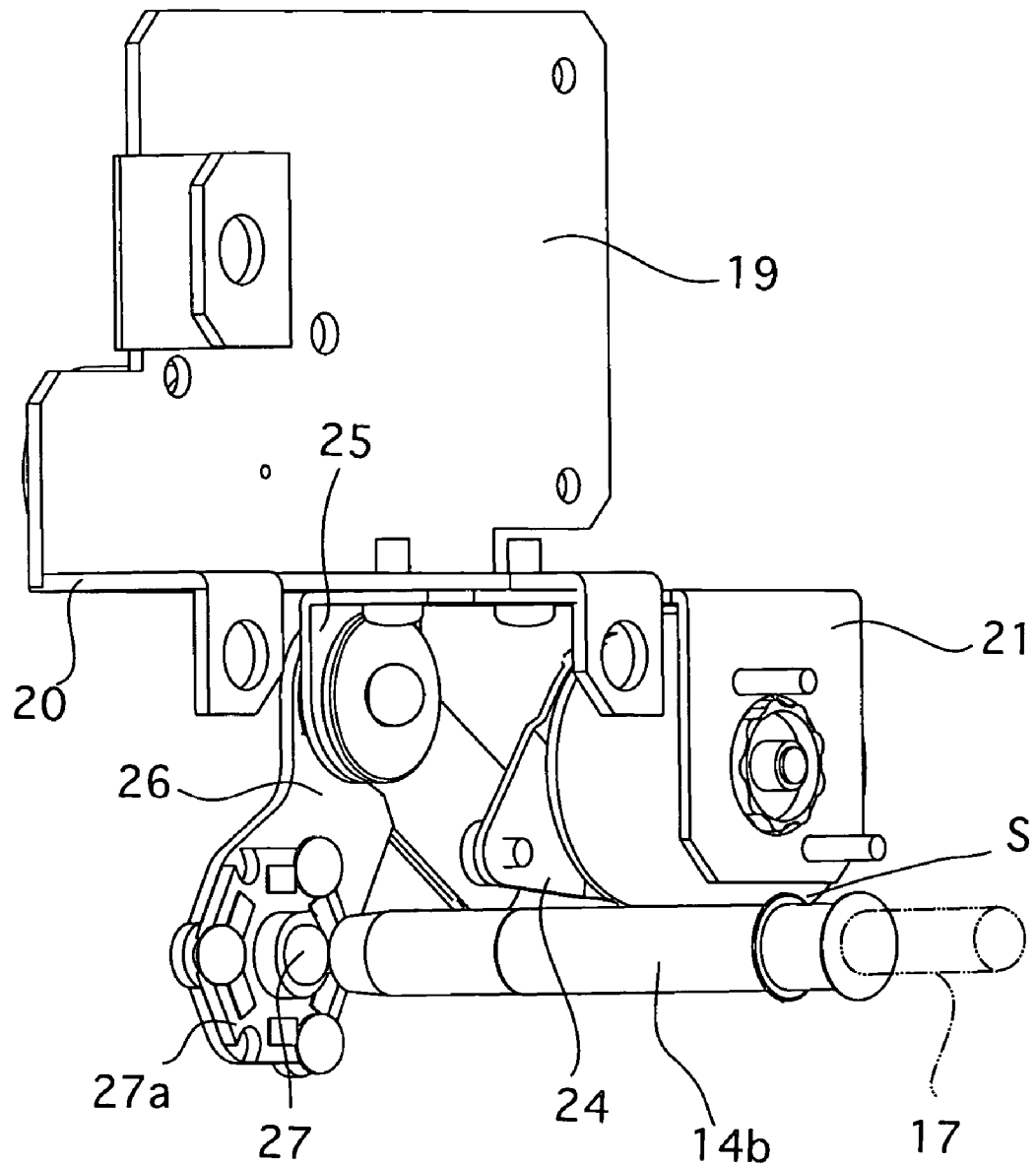
FIG. 5 is a perspective view of the auxiliary lighting device shown in FIG. 2, seen from the side of the fiber-optic light guide, in a state where the rotatable plate is in an operational position.
Figure 6:
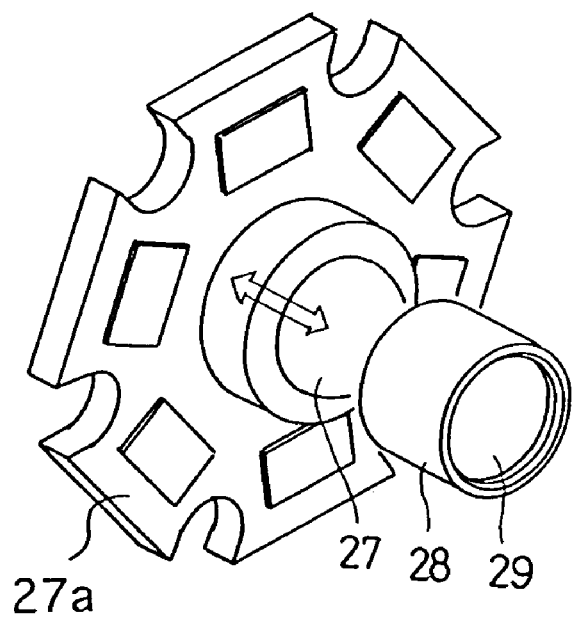
FIG. 6 is an exploded perspective view of a fundamental portion of the auxiliary lighting device, shown in FIG. 2, having an LED holder, a white LED supported by the LED holder, a lens holder and a positive lens held by the lens holder.

The auxiliary lighting device 18 is provided with an L-shaped rotary plate 26 which lies on a plane parallel to the fixing plate 19. The rotary plate 26 has a pivotal hole 26a which is fitted on the pivot 25a so that the rotary plate 26 can freely rotate about the pivot 25a. The rotary plate 26 is provided at one end thereof with an elongated slot 26b a middle portion of which is bent as shown in FIG. 3. The elongated slot 26b is engaged with an arm pivot 23a which is provided on the arm portion 24 of the rotatable member 22. As shown in FIGS. 4 through 6, the auxiliary lighting device 18 is provided with an LED holder 27a which holds a white LED (auxiliary light source) 27 at a center of the LED holder 27a. The LED holder 27a is fixed to a front surface (the surface on the side of the fiber-optic light guide 17) of the other end of the rotary plate 26. The white LED 27 serves as an auxiliary light source which is connected to the aforementioned controller provided in the auxiliary lighting device 18. The fixing plate 19, the rotary solenoid S, the rotatable member 22 and the rotary plate 26 constitute a moving mechanism for moving the white LED 27 between an operating position (the position shown in FIG. 5) and a retracted position (the position shown in FIG. 4).

Figure 2:
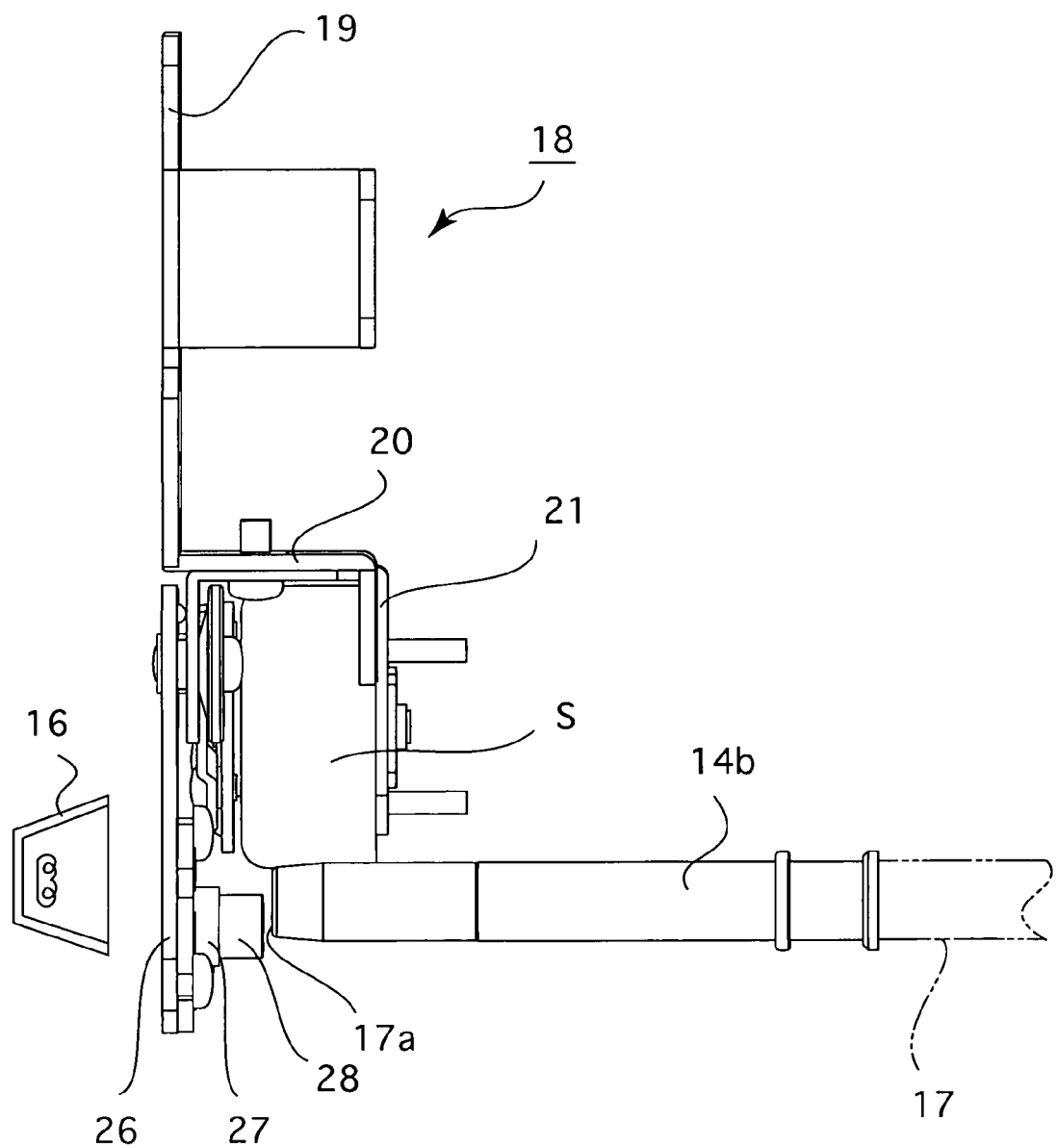
FIG. 2 is a side elevational view of an auxiliary lighting device provided in the video processor shown in FIG. 1, showing the structure of the auxiliary lighting device in relation to a main lamp and the incident end face of a fiber-optic light guide.

A lens holder 28 which holds a positive lens 29 is fixed to the front of the LED holder 27a so that the optical axis of the positive lens 29 is coincident with the optical axis of the white LED 27 having a predetermined distance therebetween along the optical axis (see FIGS. 2, 6, 7). Note that the lens holder 28 which holds the positive lens 29 is not shown in FIGS. 4, 5 and 7. The positive lens 29 has a light-gathering power which is determined in consideration of the numerical aperture (NA) of the fiber-optic light guide 17 so that the fiber-optic light guide 17 can receive almost all the light rays emitted from the white LED 27 through the incident end face 17a. The following conditions (1), (2) and (3) are satisfied:

$$r_1 \geq b \times \tan \theta_1 \quad (1)$$

$$(a-c)\tan\theta_2 = r_2 \quad (2)$$

$$\theta_3 \geq \theta_2 \quad (3)$$

wherein "a" represents the image distance of the positive lens 29;
"b" designates the object distance of the positive lens 29;
"c" designates the distance between a principle plane of the positive lens 29 and the incident end face 17a of the fiber-optic light guide 17;
"$r_1$" designates the radius of the positive lens 29;
"$r_2$" designates the radius of the incident end face 17a of the fiber-optic light guide 17;
"$\theta_1$" designates the exit angle of the light rays emitted from the white LED 27;
"$\theta_2$" designates the angle of incidence of the light rays which emerge from the positive lens 29 to be incident on the incident end face 17a of the fiber-optic light guide 17; and
"$\theta_3$" designates the threshold angle of incidence of the light rays on the incident end face 17a which are transmittable through the fiber-optic light guide 17.

Figure 9:
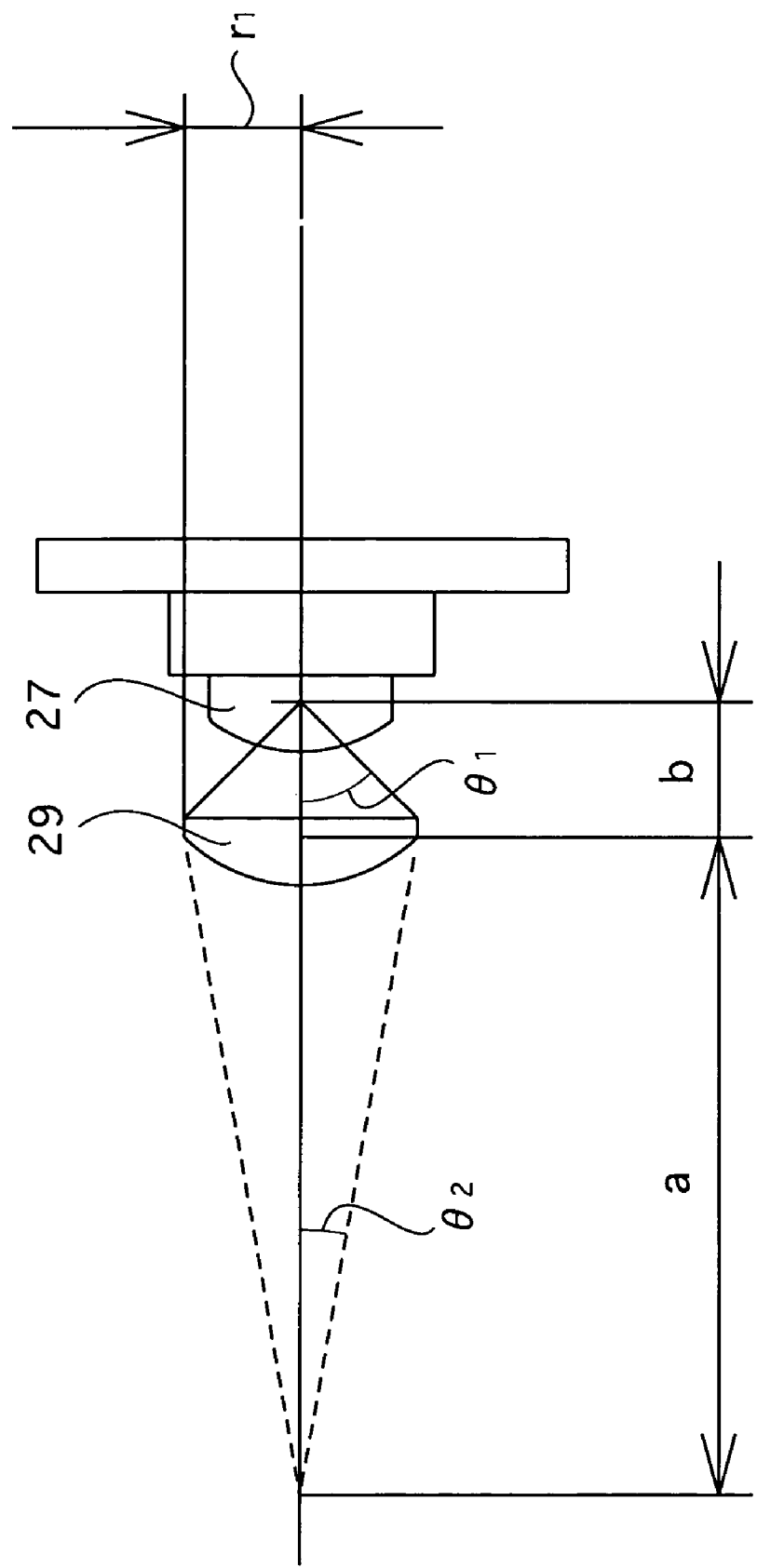
FIG. 9 is a conceptual diagram showing the relationship among the object distance of the positive lens, the image distance of the positive lens, the angle of incidence of the light rays which emerge from the positive lens to be incident on the incident end face of the fiber-optic light guide, the radius of a principle plane of the positive lens, and the exit angle of the light rays emitted from the white LED.
Figure 10:
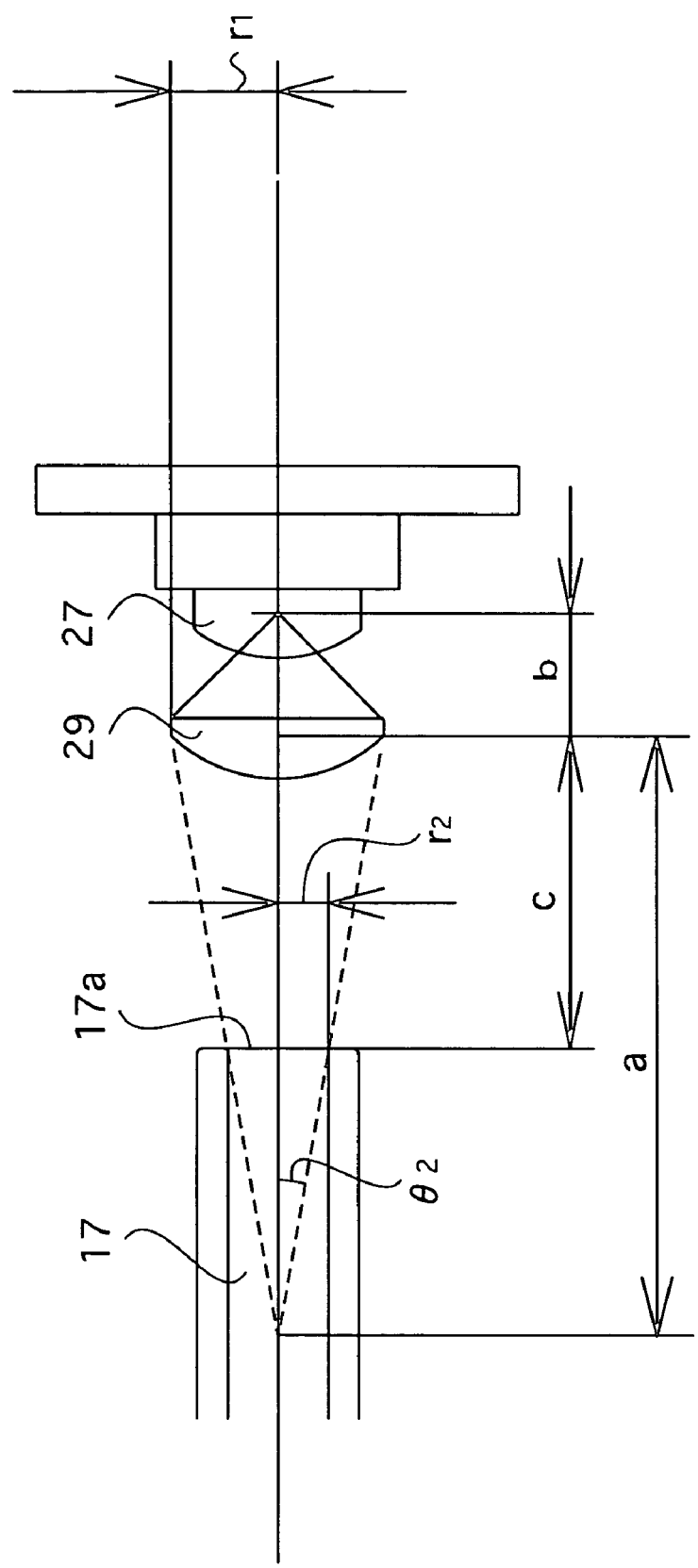
FIG. 10 is a conceptual diagram showing the relationship among the radius of the light rays which emerge from the positive lens to enter the incident end face of the fiber-optic light guide, the radius of the incident end face of the fiber-optic light guide and the distance between the principle plane of the positive lens and the incident end face of the fiber-optic light guide.

The meanings of the above three conditions (1), (2) and (3) will be hereinafter discussed with reference to FIGS. 9 and 10.

[Condition (1)]
If condition (1) is satisfied, the positive lens 29 can receive all the light rays emitted from the white LED 27.

[Condition (2)]
The angle of incidence $\theta_2$ of the light rays which emerge from the positive lens 29 to be incident on the incident end face 17a of the fiber-optic light guide 17 is determined by the exit angle $\theta_1$ of the light rays emitted from the white LED 27, the object distance b of the positive lens 29 and a focal length f which is characteristic of the positive lens 29. The exit angle $\theta_1$ is a characteristic value of the white LED 27. Since the radius "$(a-c)\tan\theta_1$" of the light rays at the incident end surface 17a which emerge from the positive lens 29 to be incident on the incident end surface 17a is determined if the aforementioned values "a", "c" and "$\theta_2$" are determined, the radius "$(a-c)\tan\theta_2$" can be made to be equal to the aforementioned radius "$r_2$" by adjusting the aforementioned distance "c". This makes it possible for the fiber-optic light guide 17 to capture light rays emerging from the positive lens 29 with efficiency.

The image distance "a" of the positive lens 29 can be determined from the following condition (4) if the positive lens 29 is regarded as a thin lens:

$$-1/a + 1/b = 1/f \quad (4)$$

wherein "f" represents the focal length of the positive lens 29.

Since the focal length f of the positive lens 29 is a characteristic value of the positive lens 29, the image distance "a" of the positive lens 29 can be determined from the object distance "b" and the focal length "f" of the positive lens 29 by condition (4) if the object distance "b" of the positive lens 29 is determined.

[Condition (3)]
The angle of incidence $\theta_2$ needs to be smaller than the threshold angle of incidence $\theta_3$ as shown in condition (3) to make it possible to guide the light rays which enter the fiber-optic light guide 17 through the incident end face 17a thereof to the exit end face of the fiber-optic light guide 17.

Even if there is an error between a design value and an actual value of the distance "c" between a principle plane of the positive lens 29 and the incident end face 17a of the fiber-optic light guide 17, the diameter of the light rays at the incident end surface 17a which emerge from the positive lens 29 to be incident on the incident end surface 17a is invariable, which is a definite advantage if the positive lens 29 is a collimating lens for changing the incident light rays into parallel rays of light, and if the effective aperture of the positive lens 29 is identical to the diameter of the incident end surface 17a of the fiber-optic light guide 17 and that the ftont focus (the focal point on the white LED 27 side) of the positive lens 29 is coincident with the point of light emission of the white LED 27.

During light emission of the main lamp 16, the white LED 27 remains OFF while the rotary solenoid S is in a non-operational state. Therefore, when the main lamp 16 is ON, the L-shaped rotary plate 26 is in anon-operational position thereof as shown in FIG. 4, while the white LED 27 is in the retracted position thereof in which the white LED 27 is aside from a point at which the white LED 27 faces the incident end face 17a of the fiber-optic light guide 17.

If the main lamp 16 goes out accidentally, a detector circuit (not shown) connected to the aforementioned controller that is provided in the auxiliary lighting device 18 detects this failure in the main lamp 16. Upon this detection by the detector circuit, the controller switches ON the white LED 27 and actuates the rotary solenoid S at the same time. Upon the commencement of operation of the rotary solenoid S, the rotary plate 26 rotates about the pivot 25a clockwise as viewed in FIG. 4 to move from the non-operational position shown in FIG. 4 to an operational position shown in FIG. 5.

The movement of the rotary plate 26 from the non-operational position to the operational position causes the respective optical axes of the positive lens 29 and the white LED 27 to be coincident with an axis of the fiber-optic light guide 17 as shown in FIG. 7. The light rays which are emitted from the white LED 27 to be incident on the positive lens 29 are converged with the angle of incidence "$\theta_2$" through the positive lens 29 so that almost all the light rays which are passed through the positive lens 29 enter the fiber-optic light guide 17 through the incident end face 17a because the diameter of the light rays at the incident end surface 17a which emerge from the positive lens 29 to be incident on the incident end surface 17a becomes substantially the same as the diameter (2r) of the incident end face 17a.

If the video processor 15 is turned OFF after the flexible insertion portion 12 is fully removed from an internal body cavity, or an internal cavity inside a machine, etc., the white LED 27 is automatically switched OFF while the rotary solenoid S is automatically moved to its initial position to retract the white LED 27 to the retracted position.

As can be understood from the above descriptions, according to the above illustrated embodiment of the video endoscope system, the service life of the auxiliary light source is semipermanent, and the power consumption of the auxiliary light source can be minimized since a white LED is adopted as the auxiliary light source of the auxiliary lighting device. Moreover, the auxiliary lighting device 18 can be designed to be smaller than that in which a light source such as a xenon lamp is used to serve as an auxiliary light source since a white LED is smaller than an ordinary xenon lamp.

Figure 8:
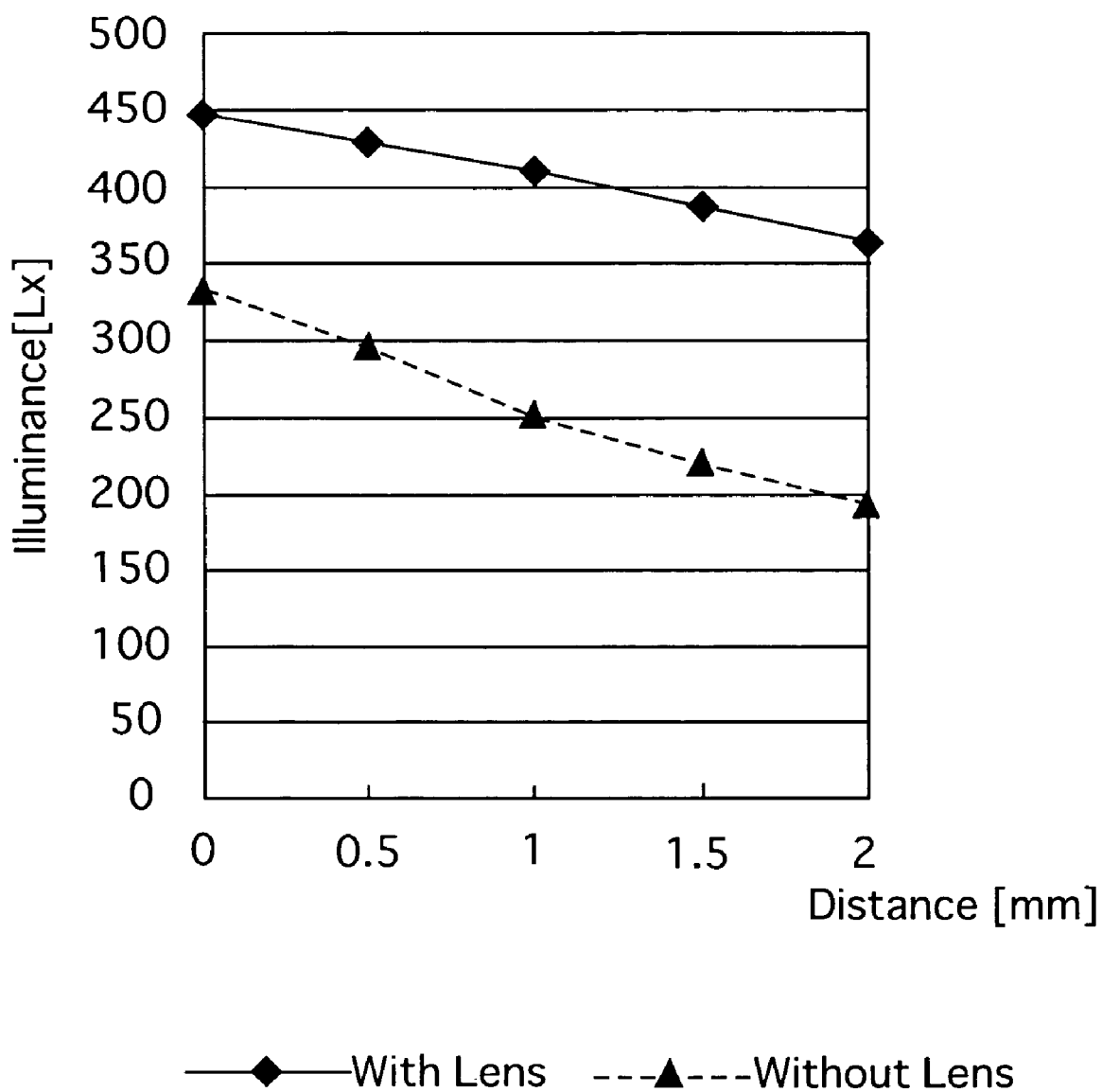
FIG. 8 is a graph showing the relationship between the illuminance of the light which emerges from the exit end face of the fiber-optic light guide and the distance between the white LED and the incident end face of the fiber-optic light guide.

In the above illustrated embodiment of the video endoscope system, there is almost no waste of the light rays emitted from the white LED 27 because of the above described arrangement wherein the positive lens 29 is positioned between the white LED 27 and the incident end face 17a of the fiber-optic light guide 17, wherein the light rays emitted from the white LED 27 are made to pass through the positive lens 29, and wherein almost all the light rays which are passed through the positive lens 29 are made to enter the fiber-optic light guide 17 through the incident end face 17a with the angle of incidence $\theta_2$. Accordingly, a sufficient quantity of light for auxiliary light can be obtained even though the white LED 27, the intensity thereof being lower than the intensity of a xenon lamp, is used as the auxiliary light source of the auxiliary lighting device 18. FIG. 8 is a graph showing the relationship between the illuminance of the light which emerges from the exit end face of the fiber-optic light guide 17 and the distance between the white LED 27 and the incident end face 17a of the fiber-optic light guide 17. It can be seen from this graph that the illuminance of the light which emerges from the exit end face of the fiber-optic light guide 17 in the presence of the positive lens 29 is much greater than that in the absence of the positive lens 29.

As can be understood from the foregoing, according to the present invention, an endoscope system having an auxiliary lighting device, wherein the service life of the auxiliary light source is semipermanent and wherein the power consumption of the auxiliary light source can be minimized while a sufficient light quantity is ensured, is achieved.

Obvious changes may be made in the specific embodiment of the present invention described herein, such modifications being within the spirit and scope of the invention claimed. It is indicated that all matter contained herein is illustrative and does not limit the scope of the present invention.

What is claimed is:

1. An endoscope system comprising:
    an endoscope having an insertion tube;
    a main light source;
    an auxiliary light source comprising a white LED; and
    a fiber-optic light guide provided in said insertion tube, said fiber-optic light guide being provided with an incident end face which selectively faces one of said main light source and said auxiliary light source, and an exit end face which faces an illuminating optical system provided at a distal end of said insertion tube, said incident end face of the fiber-optic light guide normally facing said main light source and facing said auxiliary light source in the event of failure of said main light source,
    wherein said auxiliary light source is movable between a retracted position where said auxiliary light source is spaced from a position at which said auxiliary light source faces said incident end face of said fiber-optic light guide, and an operating position where said auxiliary light source faces said incident end face of said fiber-optic light guide, said auxiliary light source remaining in said retracted position when said main light source is ON and moving to said operating position in the event of failure of said main light source,
    wherein a positive lens is positioned in front of said white LED so that said positive lens is positioned between said white LED and said incident end face of said fiber-optic light guide when said white LED is in said operating position, and in which light rays emitted from said white LED are converged through said positive lens to be incident on said incident end face of said fiber-optic light guide, such that an optical axis of said white LED is coincident with both an optical axis of said positive lens and an axis of said fiber-optic light guide when said white LED is in said operating position, and wherein the following relationships are satisfied:

$r_1 \geq b \times \tan \theta_1$ $(a-c)\tan\theta_2 = r_2$ $\theta_3 \geq \theta_2$ wherein "a" designates the image distance of said positive lens;
"b" designates the object distance of said positive lens;
"c" designates the distance between a principle plane of said positive lens and said incident end face of said fiber-optic light guide;
"$r_1$" designates the radius of said positive lens;
"$r_2$" designates the radius of said incident end face of said fiber-optic light guide;
"$\theta_1$" designates the exit angle of said light rays emitted from said white LED;
"$\theta_2$" designates the angle of incidence of light rays which emerge from said positive lens to be incident on said incident end face of said fiber-optic light guide; and
"$\theta_3$" designates the threshold angle of incidence of light rays on said incident end face which are transmittable through said fiber-optic light guide.

2. The endoscope system according to claim 1, wherein a front focus of said positive lens is coincident with a point of light emission of said white LED.

3. The endoscope system according to claim 1, wherein an effective aperture of said positive lens is equal to a diameter of said incident end surface of said fiber-optic light guide; and
wherein a front focus of said positive lens is coincident with a point of light emission of said white LED.

4. The endoscope system according to claim 1, further comprising a video processor in which said main light source and said auxiliary light source are provided.

5. The endoscope system according to claim 4, wherein said video processor comprises a moving device for moving said white LED between said retracted position and said operating position.

6. An endoscope system comprising:
an endoscope having an insertion tube; and
a lighting system having a main lamp and a white LED serving as an auxiliary lamp,
wherein said endoscope includes a fiber-optic light guide provided in said insertion tube, an incident end face of said fiber-optic light guide normally facing said main lamp when a distal end of said insertion tube is plugged into a socket provided on said lighting system,
wherein said lighting system includes a moving device for moving said white LED between a retracted position where said white LED is spaced from a position at which said white LED faces said incident end face of said fiber-optic light guide and an operating position where said white LED faces said incident end face of said fiber-optic light guide,
wherein said white LED remains in said retracted position when said main lamp is ON,
wherein said moving device moves said white LED from said retracted position to said operating position in the event of failure in said main lamp,
wherein a positive lens is positioned in front of said white LED so that said positive lens is positioned between said white LED and said incident end face of said fiber-optic light guide when said white LED is in said operating position, and in which light rays emitted from said white LED are converged through said positive lens to be incident on said incident end face of said fiber-optic light guide, such that an optical axis of said white LED is coincident with both an optical axis of said positive lens and an axis of said fiber-optic light guide when said white LED is in said operating position, and wherein the following relationships are satisfied;

$r_1 \geq b \times \tan \theta_1$ $(a-c)\tan\theta_2 = r_2$ $\theta_3 \geq \theta_2$ wherein "a" designates the image distance of said positive lens;
"b" designates the object distance of said positive lens;
"c" designates the distance between a principle plane of said positive lens and said incident end face of said fiber-optic light guide;
"$r_1$" designates the radius of said positive lens;
"$r_2$" designates the radius of said incident end face of said fiber-optic light guide;
"$\theta_1$" designates the exit angle of said light rays emitted from said white LED;
"$\theta_2$" designates the angle of incidence of light rays which emerge from said positive lens to be incident on said incident end face of said fiber-optic light guide; and
"$\theta_3$" designates the threshold angle of incidence of light rays on said incident end face which are transmittable through said fiber-optic light guide.

7. The endoscope system according to claim 6, wherein said lighting system is incorporated in a video processor.

8. The endoscope system according to claim 6, wherein an effective aperture of said positive lens is equal to a diameter of said incident end surface of said fiber-optic light guide; and
wherein a front focus of said positive lens is coincident with a point of light emission of said white LED.

9. An endoscope system comprising;
an endoscope having an insertion tube;
a main light source;
an auxiliary light source comprising a white LED;
a fiber-optic light guide provided in said insertion tube, said fiber-optic light guide being provided with an incident end face which selectively faces one of said main light source and said auxiliary light source, and an exit end face which faces an illuminating optical system provided at a distal end of said insertion tube,
wherein said auxiliary light source is movable between a retracted position where said auxiliary light source is spaced from a position at which said auxiliary light source faces said incident end face of said fiber-optic light guide, and an operating position where said auxiliary light source faces said incident end face of said fiber-optic light guide,
wherein a positive lens is positioned in front of said white LED so that said positive lens is positioned between said white LED and said incident end face of said fiber-optic light guide when said white LED is in said operating position, and in which light rays emitted from said white LED are converged through said positive lens to be incident on said incident end face of said fiber-optic light guide, and wherein the following relationships are satisfied;

$$r_1 \geq b \times \tan \theta_1$$

$$(a-c)\tan \theta_1 = r_2$$

$$\theta_3 \geq \theta_2$$

wherein "a" designates the image distance of said positive lens;

"b" designates the object distance of said positive lens;

"c" designates the distance between a principle plane of said positive lens and said incident end face of said fiber-optic light guide;

"$r_1$" designates the radius of said positive lens;

"$r_2$" designates the radius of said incident end face of said fiber-optic light guide;

"$\theta_1$" designates the exit angle of said light rays emitted from said white LED;

"$\theta_2$" designates the angle of incidence of light rays which emerge from said positive lens to be incident on said incident end face of said fiber-optic light guide; and "$\theta_3$" designates the threshold angle of incidence of light rays on said incident end face which are transmittable through said fiber-optic light guide.

10. The endoscope system according to claim 9, wherein an effective aperture of said positive lens is equal to a diameter of said incident end surface of said fiber-optic light guide; and wherein a front focus of said positive lens is coincident with a point of light emission of said white LED.

* * * * *